United States Patent [19]

Chopdekar et al.

[11] Patent Number: 5,663,415
[45] Date of Patent: Sep. 2, 1997

[54] PROCESS FOR PREPARING ANTIHISTAMINE TANNATES

[75] Inventors: Vilas M. Chopdekar, Edison; James R. Schleck, Somerset; Vernon A. Brown, Maplewood; Cheng Guo, Harrison, all of N.J.

[73] Assignee: Jame Fine Chemicals, Inc., Bound Brook, N.J.

[21] Appl. No.: 671,604

[22] Filed: Jun. 28, 1996

[51] Int. Cl.⁶ .................................................. C07C 69/88
[52] U.S. Cl. ............................................................ 560/68
[58] Field of Search ................................................. 560/68

[56] References Cited

U.S. PATENT DOCUMENTS 5,599,846  2/1997  Chopdekar ........................ 514/653

FOREIGN PATENT DOCUMENTS 239327  9/1996  Japan .

Primary Examiner—Porfirio Nazario-Gonzalez

[57] ABSTRACT

A process for preparing pure antihistamine tannate compositions. The antihistamine in the form of its free base is contacted with tannic acid in the presence of water for a period of time of about 5 minutes to 4 hours and at a maximum temperature such that not more than about 5 wt. % of the antihistamine tannate will be decomposed. Water is removed from the antihistamine tannate by freeze-drying.

10 Claims, No Drawings

PROCESS FOR PREPARING ANTIHISTAMINE TANNATES

FIELD OF THE INVENTION

The invention relates to a process for preparing antihistamine tannate compositions having a high level of purity, e.g. at least 90 wt. %, based on the weight of the composition, with the balance comprising primarily water.

BACKGROUND OF THE INVENTION

Antihistamine compounds in the form of their free bases as well as their salts, e.g. hydrochloride, maleate, tannate, etc. are well known. Frequently, it is desirable to utilize the antihistamine in the form of its tannate salt, because such salt is generally quite stable and may be administered in such form without any untoward side effects. Tannic acid, also known as tannin, is a well known naturally occurring substance. Commercially available tannic acid usually contains about 5 wt. % water, has a molecular weight of about 1700 and is typically produced from Turkish or Chinese nutgall.

Commercially available antihistamine tannate compositions are relatively impure. Such compositions are typically prepared by reacting the antihistamine free base with tannic acid in the presence of a volatile solvent, usually isopropanol. The yield is only fair (e.g. about 70%) and decomposition products e.g. 2–5 wt. %, and a significant amount of the volatile solvent, e.g. 6–10 wt. %, based on the weight of the composition, remains with the product and cannot be removed.

Typically, in the conventional isopropanol route, the antihistamine free base and the tannic acid will be present in the isopropanol at a concentration of about 20 wt. %, based on the weight of the reaction mixture. The reaction mixture is stirred for about one hour, while maintaining a temperature of 60°–70° C. The reaction mixture is cooled to room temperature and filtered. The precipitate is vacuum dried for an extended period of time at a temperature of 60°–80° C. A yield of product of only about 70% is obtained and the product purity will be about 85–90 wt. %, based on the weight of the composition (the impurities consist of isopropanol and decomposition products which cannot be removed).

Many antihistamine tannates, e.g. phenylephrine tannate, are heat sensitive and therefore undergo decomposition quite readily upon prolonged exposures to temperatures as low as 50° C. Accordingly, even when the solvent utilized in its preparation has a relatively high vapor pressure such as is in the case of isopropanol, it is impossible to reduce the solvent content below about 6 wt. %, based on the weight of the antihistamine tannate composition, even at reduced pressures and very mild elevated temperatures. Moreover, from an environmental point, it would be most desirable if the antihistamine tannate could be prepared such that the use of volatile solvents could be avoided.

SUMMARY OF INVENTION

It has now been found that it is possible to prepare pure antihistamine tannate compositions by a synthetic route which results in the production of compositions having a minimum purity level of at least 90 wt. %, usually at least 95 wt. % and often at least 98 wt. %, based on the weight of the composition, with a yield of at least about 90% and often with a yield in excess of 97%. The chief "impurity" present in the compositions prepared by the process of the invention is water which is present in an amount of 1–5 wt. %, based on the weight of the composition. Indeed, it has been found possible to produce antihistamine tannate compositions having a purity level of at least 99 wt. % and a water content of less than 1 wt. %, based on the weight of the composition.

Since the pure antihistamine tannate compositions prepared by the process of the invention is administered either in solid form, i.e. a pill, or as a suspension, the minimal amount of water present in the composition cannot be considered to be an impurity of the nature associated with degradation products or volatile organic compounds such as isopropanol. The dosage to be administered can be readily adjusted by taking into account the insignificant amount of water present in the composition.

DETAILS OF THE INVENTION

The process of the invention comprises the following steps:

(a) contacting an antihistamine in the form of its free base with tannic acid in the presence of water at a maximum temperature which will not cause decomposition of the antihistamine tannate to an extent of greater than about 5 wt %, based on the weight of the antihistamine tannate;

(b) allowing the antihistamine to remain in contact with the tannic acid in the presence of water for a period of time in the range of about 5 minutes to 4 hours, preferably 15 minutes to 2 hours, at said maximum temperature; and (c) freeze-drying the antihistamine tannate resulting from step (b) at a temperature and at a reduced pressure and for such period of time that (i) at least about 90 wt. % of the water is removed from the antihistamine tannate and (ii) decomposition of the antihistamine tannate will be limited to a maximum of about 5 wt. %.

In the event that the antihistamine is present as the salt, e.g. the hydrochloride, it is dissolved in cold water and neutralized with a stoichiometric amount of a base such as sodium or potassium hydroxide. The antihistamine free base precipitates out, recovered by filtration, washed with cold water until all chloride salts have been removed, and air dried at ambient temperatures.

The molar ratio of antihistamine free base to tannic acid will generally be in the range of about 4:1 to 6:1, but is preferably stoichiometric, i.e. 5:1, although such ratio may vary somewhat since tannic acid is a complex substance which varies from batch to batch. The exact molar ratio to be used for a given batch of tannic acid may be readily determined by one skilled in the art by preparing small aliquot samples having variations within the 4:1 to 6:1 molar ratio and determining the exact molar ratio to be used after working up the product such that neither excess antihistamine free base nor excess tannic acid will be present in the final product.

The maximum temperature of the reaction mixture (antihistamine free base, tannic acid and water) will vary depending on the particular antihistamine and its heat sensitivity. Best results will be achieved by conducting the reaction at ambient temperatures, e.g. 20°–30° C.; if the reaction between the desired antihistamine free base and the tannic acid is unduly slow, the temperature may be elevated to a maximum of that which will not cause any significant degradation (e.g. less than about 5 wt. %) of the antihistamine tannate.

The antihistamine to be reacted with the tannic acid is selected from the group consisting of phenylephrine, carbetapentane, pyrilamine, chlorpheniramine, ephedrine, pseudoephedrine, brompheniramine, bromodiphenhydramine, diphenhydramine, pheniramine, phenyltoxamine, clemastine, tripelennamine, cyproheptadine, phenindamine and phenyltoloxamine. Phenylephrine tannate is a heat-sensitive compound, and, as such, will benefit from its preparation by the process of the invention.

The water is removed from the reaction mixture by freeze-drying, a well known technique for removing water from compositions. Although freeze-drying to remove the water is a time-consuming process (one liter of reaction mixture containing one liter of water will typically take 30–36 hours to remove about 97 wt. % of the water present in the reaction mixture), it has been found to be the only method for removing water from heat-sensitive antihistamine tannate compositions without any significant formation of decomposition products. While volatile organic solvents such as isopropanol may be more quickly removed by evaporation at reduced pressures and elevated temperatures, there will always be impurities, i.e. isopropanol and decomposition products, in the product which cannot be removed without further degradation of the product. Moreover, the process of the invention will result in a yield of at least about 90%, versus the typical yield of about 70% obtained from the isopropanol route.

The freeze-drying of the reaction mixture resulting from step (b) will typically be carried out at a reduced pressure and reduced temperature, e.g. a pressure of not greater than about 500 milliTorre, preferably 300 to 100 milliTorre and at a temperature in the range of about −60° C. to −20° C., preferably −50° to −40° C. The desired end point of the freeze-drying process may be determined by condensing and measuring the quantity of water vapor removed during the freeze-drying process. The time required for completion of the freeze-drying process will vary depending on factors such as pressure, temperature, quantity to be freeze-dried, desired level of water to be tolerated in the final product, the thickness and surface area of the reaction mixture layers in the trays of the freeze-drying equipment, etc.

Steps (a) and (b) may be effected my any type of desired mixing, such as conventional stirrers. Upon allowing the reaction mixture resulting from step (b) to stand, it will be noticed that two layers will form. To insure that as much antihistamine tannate product as possible is recovered, it is preferred that the entire mass of reaction mixture resulting from step (b) be subjected to freeze-drying.

The following nonlimiting examples will serve to illustrate the present invention. These examples were carried out using phenylephrine free base as the antihistamine. Phenylephrine is a histamine which is frequently administered in the form of its tannate and it is quite heat-sensitive, i.e. prolonged exposures to temperatures as low as 50° C. will cause significant decomposition of the product. Phenylephrine as the free base has a melting point of 169°–172° C. and may be prepared from m-hydroxy-ω-chloroacetophenone and methyl-amine, see U.S. Pat. Nos. 1,932,947 and 1,954,389.

EXAMPLE 1

(Comparative Example)

In this example, phenylephrine tannate was synthesized by the isopropanol route for comparative purposes. A reaction vessel consisting of a 2-liter, 3-neck flask was set up with a thermometer, stirrer, condenser and heating mantle. 20 g phenylephrine free base and 400 g isopropanol were added to the flask and the contents were heated, with stirring, to 65°–70° C. in order to dissolve the phenylephrine base. A separate solution of 43.2 g of tannic acid (mol. wt. of about 1700) in 400 g isopropanol was prepared and heated to 40° C., with stirring.

The tannic acid solution was slowly added, with stirring, to the reaction vessel over a period of about 30 minutes, while maintaining the contents of the reaction vessel at a temperature of about 70° C. The reaction mixture was stirred for about 60 minutes, while maintaining a temperature of about 70° C. and was thereafter cooled to about 15° C. The phenylephrine tannate product was recovered from the reaction mixture by filtration and was then washed with 50 g of isopropanol.

The phenylephrine product was then vacuum dried at about 1 mm Hg pressure and at about 60° C. temperature over a period of about 60 minutes. The yield of product was 45.5 g (72% yield) and its density was 0.45 g/cc. GC and HPLC analysis indicated that the product contained about 8 wt. % isopropanol and about 2 wt. % of degradation products. All efforts to remove the isopropanol and degradation products by further prolonged vacuum drying failed.

EXAMPLE 2

Phenylephrine tannate was synthesized by the process of the invention as follows. In a 5-liter flask were placed 680 g tannic acid (mol. wt. of about 1700) in 1 kg water. The temperature of the solution was ambient (about 22° C.) and, while stirring, 320 g phenylephrine free base were added to the flask over a 15-minute period. Stirring was continued for an additional 2 hours. Upon allowing the reaction mixture to stand, it was noted that two layers had formed.

The entire mass of the reaction mixture was then freeze-dried at a reduced pressure of 200–100 milliTorre and a temperature of −50° to −40° C. for about 36 hours. At this point, the water which had been removed was condensed and its weight equalled about 1 kg. The dried phenylephrine base was found to contain 2 wt. % of water and it had a density of 0.8 g/cc. Analysis of the product by HPLC showed no discernible amounts of materials other than phenylephrine tannate and water. The overall yield of product was 96%.

What is claimed is:

1. A process for preparing an antihistamine tannate composition which comprises the steps of:
   (a) contacting an antihistamine in the form of its free base with tannic acid in the presence of water at a maximum temperature which will not cause decomposition of the antihistamine tannate to an extent of greater than about 5 wt %, based on the weight of the antihistamine tannate;
   (b) allowing the antihistamine to remain in contact with the tannic acid in the presence of water for a period of time in the range of about 5 minutes to 4 hours at said maximum temperature; and
   (c) freeze-drying the antihistamine tannate resulting from step (b) at a temperature and at a reduced pressure and for such period of time that (i) at least about 90 wt. % of the water is removed from the antihistamine tannate and (ii) decomposition of the antihistamine tannate will be limited to a maximum of about 5 wt. %.

2. The process of claim 1 wherein the antihistamine is selected from the group consisting of phenylephrine, carbetapentane, pyrilamine, chlorpheniramine, ephedrine, pseudoephedrine, brompheniramine, bromodiphenhydramine, diphenhydramine, pheniramine, phenyltoxamine, clemastine, tripelennamine, cyproheptadine, phenindamine and phenyltoloxamine.

3. The process of claim 2 wherein the antihistamine comprises phenylephrine.

4. The process of claim 1 wherein the molar ratio of the tannic acid to the antihistamine is in the range of about 4:1 to 6:1.

5. The process of claim 1 wherein the water is present in an amount such that the weight ratio of tannic acid to water is in the range of 1:10 to 10:1.

6. The process of claim 1 wherein the contact time in step (b) is in the range of 15 minutes to 2 hours.

7. The process of claim 1 wherein the freeze-drying is carried out at a pressure of not greater than about 500 milliTorre and at a temperature in the range of about $-60°$ C. to $-20°$ C.

8. The process of claim 7 wherein the freeze-drying is carried out at a pressure in the range of 300 to 100 milliTorre and a temperature in the range of $-50°$ to $-40°$ C.

9. The process of claim 1 wherein the entire mass of the reaction mixture resulting from step (b) is subjected to freeze-drying.

10. The process of claim 1 wherein steps (a) and (b) are carried out at temperatures in the range of about $20°-30°$ C.

* * * * *